United States Patent [19]

Blasnik et al.

[11] Patent Number: 4,976,721
[45] Date of Patent: Dec. 11, 1990

[54] SURGICAL CLAMPING DEVICE

[75] Inventors: William Blasnik, Englewood, N.J.; Stanley B. Pollak, Huntington, N.Y.

[73] Assignee: The Research Foundation of State University of New York, Albany, N.Y.

[21] Appl. No.: 284,073

[22] Filed: Dec. 14, 1988

[51] Int. Cl.⁵ .............................................. A61B 17/12
[52] U.S. Cl. .................................... 606/157; 24/523; 24/528; 24/564
[58] Field of Search ....................... 128/322, 325, 346; 24/522, 523, 524, 527, 528, 564; 251/7; 606/120, 157, 158

[56] References Cited

U.S. PATENT DOCUMENTS

| | | | |
|---|---|---|---|
| 1,918,889 | 7/1933 | Bacon | 128/322 |
| 2,618,268 | 11/1952 | English | 128/346 X |
| 3,506,012 | 4/1970 | Brown | |
| 3,509,882 | 5/1970 | Blake | 128/346 X |
| 3,510,923 | 5/1970 | Blake | 128/346 X |
| 3,608,554 | 9/1971 | McGuinness | 128/346 X |
| 4,324,248 | 4/1982 | Perlin | |
| 4,407,285 | 10/1983 | Perlin | |
| 4,844,066 | 7/1989 | Stein | 128/346 |

Primary Examiner—Michael H. Thaler
Attorney, Agent, or Firm—Hoffman & Baron

[57] ABSTRACT

An intestinal occluding clamp including first and second clamping members with jaws, a biasing spring, a clamp housing, a clamp base and a clamp cap. The clamp housing has a housing cavity formed at one end thereof and a first clamping member is connected to and projects away from the housing cavity. The biasing spring is disposed within the cavity and circumferentially about the base post. The clamp cap and biasing spring are retractably mounted within the housing cavity and provide a spring-loaded, push-button housing for simple and reliable operation. Take-up clearances within the housing are provided such that when the cap is fully depressed downwardly with one's thumb, the distal ends of the jaws first move apart until the clamp is in locked-open position with no spring resistance against the surgeon's thumb, and when the clamp is released, the clamping members move towards each other during spring-biased forced closing movement, and finally the jaws become substantially parallel with the tubular structure, interposed therebetween. Another aspect of the present invention is an intestinal occluding clamp with first and second corrugated surfaces having anti-slip grooves which facilitate sliding of an intestine between the open clamping members with minimal degree of resistance or reacting force and, provides essentially high resistance to movement of clamped vessel's out from between the substantially parallel, closed clamping members.

17 Claims, 8 Drawing Sheets

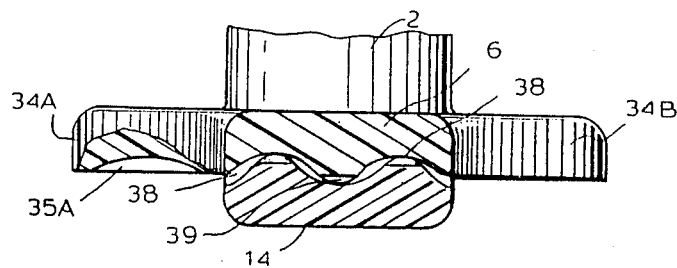
Fig. 8A
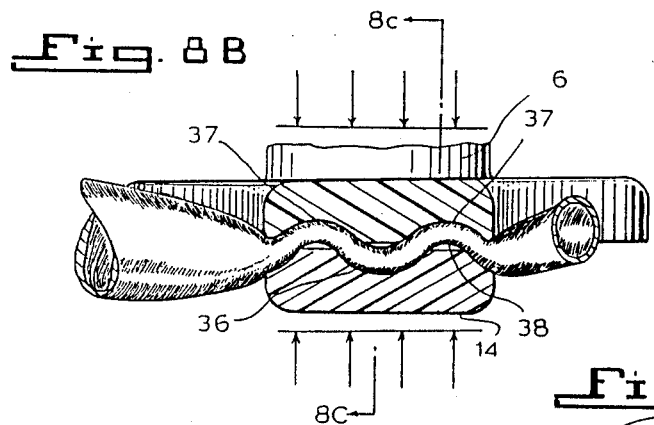
Fig. 8B
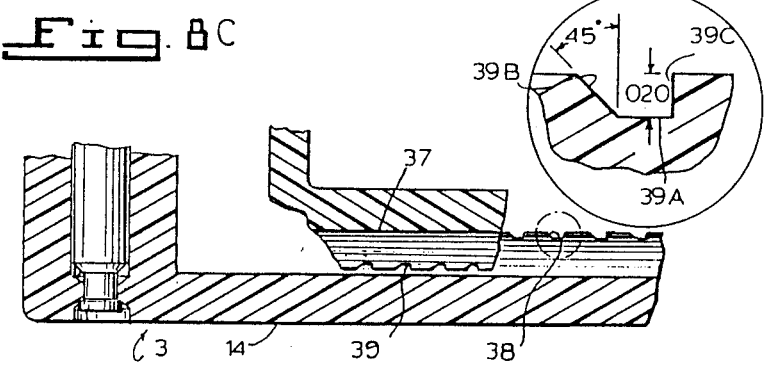
Fig. 8C
Fig. 8D

SURGICAL CLAMPING DEVICE

BACKGROUND OF THE INVENTION

The present invention relates generally to surgical clamping devices of the type used to occlude or otherwise seal off tubular structures, such as intestines, during surgical procedures. More particularly, the present invention relates to surgical clamping devices which can occlude tubular structures under uniformly distributed clamping pressure, thereby preventing leakage of matter therethrough.

At some point during most intestinal operations, it is necessary to actually open the intestine and expose the intestinal lumen, the interior channel of the intestine. To prevent the escape of intestinal contents, the surgeon usually places a clamp (e.g. an intestinal forcep) across the intestine above and below the area that will be opened. A variety of forceps are available for this purpose, including the Kocher, the Mayo-Robson and the Doyen intestinal forceps. Like conventional forceps, these clamping devices operate in a scissor-like fashion. One principal shortcoming with such types of clamping devices is that, when conventional forceps open with a pivotal movement, they are not in parallelism in the clamped position on the tubular structure. Thus, one side of the vessel may be damaged by pinching it excessively hard in order to completely occlude the opposite side thereof.

The existing intestinal forceps have several other characteristics which make them unsatisfactory to a large number of practicing surgeons. These instruments are all approximately 10 inches in length, 5 inches of which are the handles. This excessive length causes the instruments to be unwieldy and to obstruct the surgeon's work area while they are being used. In addition, the clamping pressure distribution provided along the clamping members of the forceps is not uniform, as illustrated in FIG. 1A.

Although this type of clamp is considered to be "atraumatic" and is intended to occlude the intestine without injuring it, in actual use these instruments are quite capable of traumatizing the intestinal tissue which they clamp, the result of which is to cause tissue cells to die. In an effort to reduce the amount of trauma caused by these clamps, many surgeons slip pieces of soft rubber tubing over the clamp members. This practice is so widespread that the generally recognized name for these intestinal forceps is "rubber shods".

These problems have led surgeons to look for other ways to occlude the intestine more effectively and efficiently.

Similarly, in other types of surgical operations, a considerable number of spring clips are required to occlude severed blood vessels as well as for other purposes. The most common type of spring clip has smooth surfaced swinging jaws which are parallel when closed upon themselves but which are not parallel in the partially spread position that they assume on a blood vessel. While such types of spring clips can completely occlude a blood vessel to stop bleeding, such clamping devices based on the "parallel jaw-member principle" are not suitable where the tubular structure is larger than blood vessels, for example, when the tubular structure has the dimensions of an intestine. This is because the clamping members of these types of clamping devices (i) deflect away from their parallel arrangement when an intestine is clamped therebetween, (ii) the jaws tend to slip off the intestine, and (iii) a non-uniform distribution of clamping pressure is exerted on the intestine while clamped between the deflected almost parallel jaws. This non-uniform distribution of clamping pressure is illustrated in FIG. 1B.

Prior art surgical clamping devices also suffer from inadequately designed jaw teeth, which while designed to resist slippage of the jaws on the vessel, consequently exert dissimilar force components on the vessel (i.e. the intestine) at different locations. Specifically, the occluding (i.e. clamping) pressure is not uniformly distributed, and consequently causes trauma to the intestinal tissue, the result of which can be to cause the tissue cells to die.

Various high frictional clamping surfaces have been used by prior art devices, and nearly all of such surfaces include interlocking jagged or sharp edges or teeth which penetrate or unduly deform intestinal tissue and cause trauma thereto. In short, prior art clamping surfaces create high surface pressure locations which, while securing the intestine within the clamping device, create the serious problem of traumatization to intestinal tissue and the like.

In view of the above-described problems in the surgical clamping arts, a variety of prior art surgical clamping devices exist and are known to be useful in a variety of surgical settings, yet fail to provide an effective solution to such problems. Examples of such surgical clamping devices can be found in prior art U.S. Pat. Nos. 4,324,248; 4,407,285; 3,510,923; 3,509,882; and 3,506,012, which will be briefly summarized hereinbelow.

U.S. Pat. No. 3,509,882 to Blake discloses a parallel jaw spring clip. As illustrated, two opposed jaws are each molded integrally with the inner ends of two telescopic members. One member is disclosed as being a plunger and the other member as a barrel for the plunger. A metal compression spring is contained within the plunger and barrel, and is seated on a cap. Another cap having a spring guide pin is secured in the upper end of the barrel. The upper end of the spring is positioned against the cap and is secured in the upper part of the barrel to urge the jaws toward a closed position. Thus, the jaws are separable by pinching the opposed caps, and will come back in contact with one another when the pinching pressure is relieved. However, despite the parallelism in the jaws, when there is no intestine or similarly large tubular structure therebetween, the parallel surfaces of the jaw deflect under load (e.g. clamping an intestine), and thereby change the clamping pressure along the jaws. Consequently, under loading, the clamping pressure is not uniform along the jaws from the proximal to the distal end thereof. Also, due to the resultant clamping pressure distribution and the parallel jaw closing movement and clamping configuration, there is a tendency for the jaw members to slip off the vessels to be occluded. In addition, the serrated teeth on the jaws, while creating frictional forces between the vessels and jaws, result in high pressure locations, (thus a non-uniform pressure distribution along the cross section of the jaw members), and therefore have a tendency to cause trauma to tissue.

U.S. Pat. No. 3,510,923 to Blake discloses a parallel jaw ratchet clip having two jaws which remain in parallelism throughout their opening and closing movements. The jaws are mounted on two relatively slideable members which are pinched closed in accordance with the clamping force desired by the surgeon. A ratchet device holds the jaws closed and pinch grips are provided to release the ratchet device and open the jaws. A retractor is similarly constructed but has jaws equipped with hooks instead of teeth and the ratchet action is reversed to hold the jaws open instead of closed. This surgical clamping device, however, has several significant shortcomings and drawbacks, as well. In particular, despite the parallelism in the jaws when there is no intestine clamped therebetween, the parallel surfaces of the jaw deflect under load (e.g. clamping down on an intestine), and thereby change the clamping pressure along the jaws. Consequently, under loading, the clamping pressure is not uniform along the jaws from the proximal to the distal end thereof. Also, due to the resultant clamping pressure distribution and the parallel closing movement and clamping configuration, there is a tendency for the jaw members to slip off the vessels to be occluded. In addition, the serrated teeth on the jaws, while creating frictional forces between the vessels and jaws, result in high pressure locations, (thus a non-uniform pressure distribution along the cross section of the jaw members), and therefore have a tendency to cause trauma to vessel tissue.

U.S. Pat. No. 4,324,248 to Perkin discloses a microsurgical clip for clamping small blood vessels. The microsurgical clamp includes a hollow shell having top and bottom openings with an integral clamping element (i.e. "duck bill") extending forwardly from the lower edge of its front wall. A cooperating insert of an inverted "U" shape is nested in the housing to define a central pocket and terminates in a clamping element which cooperates with the duck bill of the hollow shell. The shell and the insert have their back walls hinged together, and an expansible spring is seated in the pocket with one end coupled to the shell and the other end coupled to the insert for urging the insert upwardly into the shell to bias the clamping elements together. The insert has a crown which projects upwardly through the opening at the top of the shell so that, upon application of pinching pressure, the insert is pressed downwardly with respect to the shell to compress the spring and to spread the clamping elements for clamping engagement of a blood vessel therebetween. However, as a result of the scissor-like operation of the clamping elements, the clamping pressure is not uniform along the clamping elements from the proximal to the distal end thereof. Also, due to the resultant clamping pressure distribution and the closing movement of the clamping elements and clamping configuration, there is a tendency for the clamping elements to slip off the vessels or other tissue. In addition, without any special provision for a gripping surface to create frictional forces between the vessels and jaws, clamping elements having exceedingly high clamping pressures must be used. Thus, while not necessarily creating a non-uniform pressure distribution along the cross section of the clamping elements, there is nevertheless a great tendency to cause trauma to vessel tissue, the result of which cause the cells thereof to die. In addition, such clamping device is wholly unsuitable for occluding intestines.

U.S. Pat. No. 4,407,285 to Perkin discloses a microsurgical clip for clamping small blood vessels, as for example, during brain surgery or the like. The microsurgical clamp includes a hollow shell of generally rectangular shape having opposed side walls and a front wall, the shell having a clamping element (i.e. duck bill) or jaw, extending forwardly at the lower edge of the front wall. A cooperating insert of zigzag shape nested in the shell includes a top wall, front wall and clamping element, the insert being hinged between the side walls. An expansible spring is seated between the bottom wall of the shell and the top wall of the insert for biasing the clamping element into resilient clamping engagement. The hinge connection includes a hinge pin extending between the side walls at the upper back corners encircled by a tab bent at the end of the top wall of the insert. The side walls are angled downwardly from the hinge pin and the front wall of the shell is foreshortened so that, when the clamping elements are in clamping engagement, the insert projects upwardly beyond the shell. When the projecting insert is pinched downwardly by the finger tip, the spring is compressed accompanied by relative spreading of the clamping elements for engagement of a blood vessel therebetween. One of the features of the construction is that the back of the shell is open to provide a spring access opening for insertion of a selected spring to produce a predetermined degree of clamping force.

However, this clamping device, as with the one disclosed in U.S. Pat. No. 4,324,248, also suffers from similar shortcomings and drawbacks. Thus for example, owing to its scissor-like operation, the clamping pressure is not uniform along the length of the clamping elements, and also due to the closing movement of the clamping elements, there is a tendency for the clamping elements to slip off. In addition, the clamping force required to secure the clip onto a vessel is usually so large that trauma to tissue results. Moreover, this clamping device is wholly unsuitable for occluding intestinal lumen.

In view of the above surgical clamping devices, it is apparent that the prior art has not shown or even hinted how to achieve a surgical clamping or occluding device with a combination of features which includes (i) a clamping mechanism providing a truly uniform clamping pressure distribution along the length of the clamping members or jaws; (ii) an anti-slip clamping mechanism and/or jaw clamping surface which prevent vessels and tubular structures from slipping out of the clamping device during surgical operations, without the requirement of excessive tissue-traumatizing clamping pressures; (iii) jaw clamping surfaces which provide a uniform clamping pressure along the width-wise dimension of the clamping members and thereby prevent trauma to vessel tissue; (iv) a thumb-operable lock-open and release mechanism for easier and quicker application; (v) minimum size so as not to obstruct the surgical procedure; and (vi) manufacturability using light weight materials, having extraordinary degrees of reliability.

Accordingly, it is a primary object of the present invention to provide a surgical clamping device having a handactuatable clamping mechanism which provides a truly uniform clamping pressure distribution along the entire length of the clamping members or jaws.

Another object of the present invention is to provide a surgical clamping device having first and second clamping members, each with jaws which move from the open position to the closed position by the distal ends (i.e. tips) of the jaws meeting first, and then the jaws forceably moving towards each other reaching a parallel position when the spring force of the clamp is in equilibrium with the force of the closed intestinal lumen, wherein the distal tips of the clamping surfaces are closer than the proximal clamping surfaces, but are equally spaced when clamping is completed. As a result of this anti-slip clamping mechanism, a tubular structure such as an intestine can be completely occluded between the jaws under a uniformly distributed clamping pressure, and prevented from slipping out during surgical operations.

It is a further object of the present invention to provide such a surgical clamping device providing a uniform clamping pressure along the width-wise dimension of the clamping members and thereby prevent slippage of the clamp and trauma to vessel tissue.

An even further object of the present invention is to provide such a surgical clamping device which accomplishes complete occlusion of the vessel, is light in weight, disposable and inexpensive to manufacture.

Other and further objects of the present invention will be explained hereinafter, and will be more particularly delineated in the appended claims, and other objects of the present invention will hereinafter become apparent to one with ordinary skill in the art to which the present invention pertains.

SUMMARY OF THE INVENTION

The present invention is a surgical clamping device for occluding anatomical tubular structures such as the intestinal lumen, blood vessels, arteries and the like.

In general, the surgical clamping device comprises first and second clamping members, a biasing means, and a means for controlling the deflection of the first and second clamping members. Each clamping member has a jaw and a distal and a proximal end. The first and second clamping members are connected at their proximal ends for movement between an open position, wherein a tubular structure can be inserted therebetween, and a closed position wherein said tubular structure is clamped down and thereby completely occluded under a uniformly distributed clamping pressure.

The biasing means continually urges the jaws to the closed position, and exerts a force which is overcome by human fingers for opening the jaws. The biasing means also urges the jaws toward the closed position against the force of matter passing through the tubular structure.

A means is also provided for controlling the deflection (i.e., tilt, cant, or inclination) of at least one of the first and second clamping members during forced movement to the fully open position.

On completion of the opening operation, the distal ends of the jaws (i.e., clamping members) move apart at an acute angle and lock to allow easy placement of the tubular structure therebetween. When released from the open position, the distal ends of the jaw move towards each other during forced closing movement (if no tubular structure is interposed between clamping members) while the biasing force continues to close the proximal end. Finally the biasing force deflects the clamping jaw surfaces into parallel alignment, whereby the tubular structure is occluded under uniformly distributed clamping pressure, thereby preventing leakage of matter-or fluid therethrough. Notably, the uniformly distributed clamping pressure upon the tubular structure between the clamping members, results from take-up clearances and deflection of the clamping members under loading forces.

In the preferred embodiment, the surgical clamping device further includes a clamp housing, a clamp base and a clamp cap, the clamp housing having a housing cavity formed at one end thereof. The first clamping member is connected to and projects away from the housing cavity. The housing cavity is defined by front, side and rear walls, forming an interior housing wall-configuration, and includes a bottom wall having an aperture formed therethrough. The housing cavity has a front end in the direction of the distal end of the clamping members and a rear end in the direction away therefrom.

The clamp base has a base post orthogonally projecting away from the body of the clamp base, which forms in the preferred embodiment, the second clamping member. The base post has a bore formed therethrough and the base post passes through the bottom wall aperture of the housing when the surgical clamping device is assembled.

The clamp cap has a cap portion with a top finger recess, and a stem or shaft portion which projects from the cap portion. The cap portion has downwardly projecting front, side and rear walls, the configuration thereof being geometrically similar to the housing wall-configuration. In the preferred embodiment, the biasing means is a spring disposed within the cavity, and preferably, circumferentially about the base post. The cap stem inserts through the bore of the base post and has an enlarged flange formed at the distal end of the cap stem (i.e. after assembly), in order to prevent withdrawal of the stem from the bore. The cap wall is always in the housing cavity, and the body portion of the cap is retractably insertable into the housing cavity by pressing the cap recess downwardly with, for example, a thumb. This movement, in turn, cause the cap rear wall to become adjacent the housing rear wall, against the biasing force of the spring. This feature of the present invention provides a spring-loaded, push-button housing for simple and reliable operation.

To facilitate relative tilting of the clamping members during opening and closing operations to maximize clearance between the jaws, the clamp housing also includes in the preferred embodiment, a tilt fulcrum means, an angle ramp surface and a tapered surface about the front lip of the bottom wall aperture, whereas the cap is provided with a tilted spring seat.

Specifically, the tilt fulcrum means is disposed in the housing cavity and preferably comprises a first and second fulcrum means in the form of small, spaced-apart cylindrical structures disposed on the rear portion of housing bottom wall. A primary function of the fulcrum means is to provide cantilever or tilting action to maximize clearance between the jaws, when the bottom edge of the cap walls are pressed down into contact with the fulcrum means.

The angle ramp surface, typically a wall, is formed at the upper portion of the housing front wall and serves to force the cap stem and base post to tilt towards the rear wall as the front portion of the cap is pushed down into the housing cavity and engages the angle ramp surface.

In the preferred embodiment, the tilted spring seat is formed in the underside of the cap portion about the axis of the cap stem. This feature of the present invention causes the rear portion of the spring to be under higher compressional forces than the front portion of the spring when the cap portion is pressed down into the housing cavity. In cooperation with the fulcrum means, the tilted spring seat and spring provide greater upward force on the rear portion of the cap than on the front portion thereof, that is, with respect to the pivot point between the fulcrum means and bottom edge of cap side walls.

The tapered wall formed about the front lip of the bottom wall aperture is to provide clearance between the base post and the aperture to allow relative tilting of the base post and cap stem subassembly with respect to the bottom wall of the housing during movement of the distal end of the second clamping member towards the distal end of the first clamping member during opening operation.

The rear wall of the cap and the rear wall of the housing are shaped and spaced apart as to provide clearance to allow the cap front wall to tilt away from the housing front wall when the cap is pressed down into the housing cavity.

As a result of these above-described conditions, the cap and base subassembly is capable of tilting with respect to the clamp housing.

In order to maintain and lock the surgical clamping device in the open position when the clamping members are forcibly opened, the clamp housing further includes a lock tab, and the clamp base post includes a lock flange. Specifically, the lock tab is disposed in the bottom side of the housing adjacent the rear side of the aperture, and the lock flange is disposed on the base post such that the lock tab and lock flange lockingly interengage when the cap is pushed fully down into the housing cavity and the cap bottom tilts forward on the tilt fulcrum. Upon such interengagement, the first and second clamping members are locked in the open position. To release the clamping members from the locked "spread open" position, the rear side of the cap top is depressed, upon which the distal ends of clamping members first swing towards each other in one continuous motion, under the biasing force of the spring and the cantilever action of the fulcrum means on the bottom edge of the cap side walls.

In the preferred embodiment, the housing also includes first and second gripping tab, each of which project from opposing sides of the housing cavity. The gripping tabs have respective gripping recesses which provide two surfaces against which the surgical clamping device can be held firmly in the hand of a surgeon or surgeons' assistant while the thumb thereof presses on the cap recess to open and/or close the surgical clamping device.

Another aspect of the present invention is a clamping surface to be provided to the jaws of the clamping members of a surgical clamping device, which, in general, includes a first and second corrugated surface. Each surface has periodically recurring peaks and valleys that are matched with one another to establish an interlocking relationship. When the clamping members are disposed in a clamped position, the peaks and valleys are aligned in the longitudinal dimension of the clamping members, and serve to substantially increase the surface gripping area thereof. Preferably, the corrugated surfaces are generally "smooth" in the geometric sense, implying that there are no discontinuities in the surface.

In order to achieve a uniform clamping pressure in the width-wise direction of the clamping members, the spacing (i.e. distance) between corresponding clamping surface points on the first and second clamping members is substantially equal along the entire length and width of the clamping surface when the clamping surfaces are spaced apart by the distance equal to the height of a clamped down tubular structure.

A plurality of specially designed anti-slip grooves are formed in the peaks of the upper and lower corrugated surfaces, respectively, and serve to provide periodic recesses into which intestinal tissue can be pressed. Each anti-slip groove facilitates sliding the intestine or other vessel between the open clamping members with a minimal degree of resistance or reacting force and, on the other hand, provides substantially high resistance to movement of clamped vessels out from between the clamping member in the direction of the distal ends thereof, thus preventing the clamped vessel from slipping out of the surgical clamping device of the present invention.

The cap, base, and housing of the surgical clamping device of the present invention can be made of high tensile strength, injection-molded thermoplastic as to thereby make the device disposable and inexpensive to manufacture. Preferably, the spring is made of stainless steel, but other suitable materials may be used as well. In certain applications, the components of the surgical clamping device can be fabricated from stainless steel, which permits sterilization and reuse.

A primary advantage of the present invention is that the clamping members do not close in a conventional scissor-like or parallel manner, but nevertheless move into a parallel configuration when clamped, so as to provide truly even clamping pressure across their entire length.

Another advantage of the present invention is that the handles are completely eliminated from the device, which results in a much smaller and less cumbersome instrument that will not interfere with the surgeons' work. Also, the interlocking corrugations with the anti-slip grooves are provided on the clamp faces (i.e. jaws) to increase the surface area of contact. This feature ensures that a truly uniform clamping pressure is achieved across the width-wise dimension of the clamping surface, thereby mitigating traumatization of tissue under clamping pressure. Also, slipping of vessels out from between closed clamping members is completely prevented.

In addition, since the clamping device of the present invention closes with a force determined by the selection of the spring, the clamping pressure can be preselected at a correct level and remains reasonably constant over a range of application thicknesses.

DESCRIPTION OF THE DRAWINGS

For a further understanding of the objects of the present invention, reference is made to the following detailed description of the preferred embodiment which is to be taken in connection with the accompanying drawings, wherein:

FIG. 8A is an elevated cross-sectional end view of the first and second clamping members and respective clamping surfaces of the present invention, shown in a closed position without a tubular structure clamped therebetween;

FIG. 8B is an elevated cross-sectional end view of the first and second clamping members and respective clamping surfaces of the present invention, shown in a clamped position with a tubular structure such as an intestine clamped therebetween;

FIG. 8C is an elevated side view of the clamping surfaces of the present invention, showing anti-slip grooves formed in the peaks of the interlocking corrugated clamping surfaces;

FIG. 8D is a side elevational enlarged cross-sectional view of the clamping members showing the anti-slip grooves formed in the peaks of the corrugated clamping surfaces;

DETAILED DESCRIPTION OF THE PREFERRED EMBODIMENT

Figure 1A:
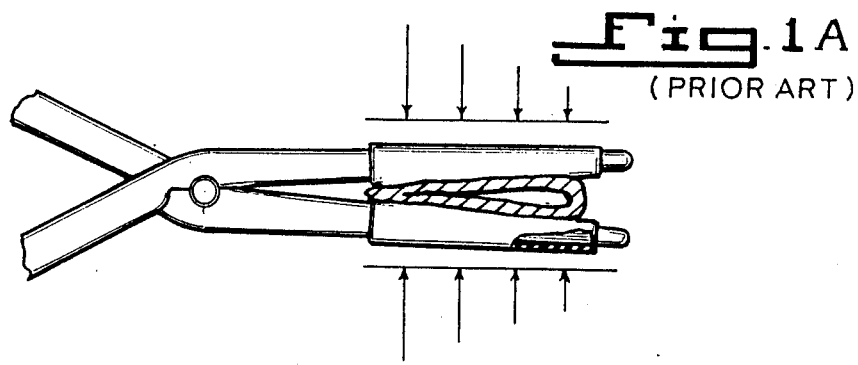
FIG. 1A is an elevational side view of a prior art scissor-like clamping forcep which is characterized by a clamping pressure distribution that is too strong near the pivot point and too weak at the distal end of the closed clamping members.
Figure 1B:
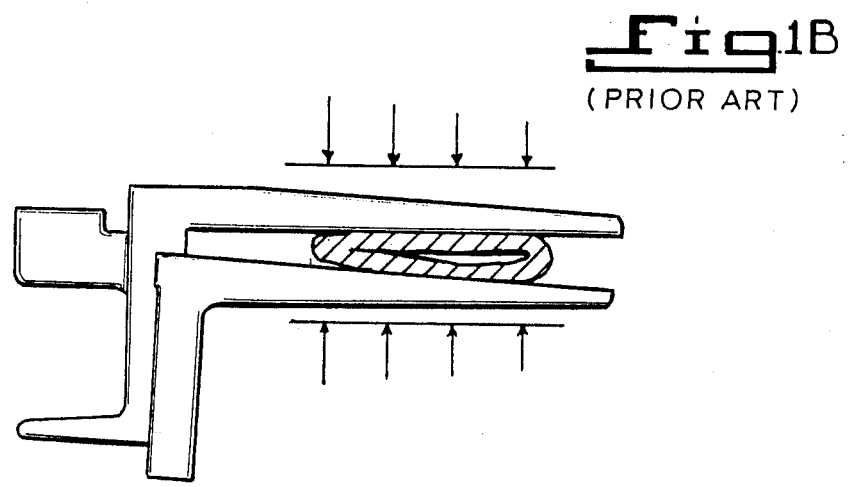
FIG. 1B is an elevational side view of a prior art parallel closing and opening surgical clamping device characterized by a clamping pressure distribution that decreases along the length of the closed clamping member.
Figure 2:
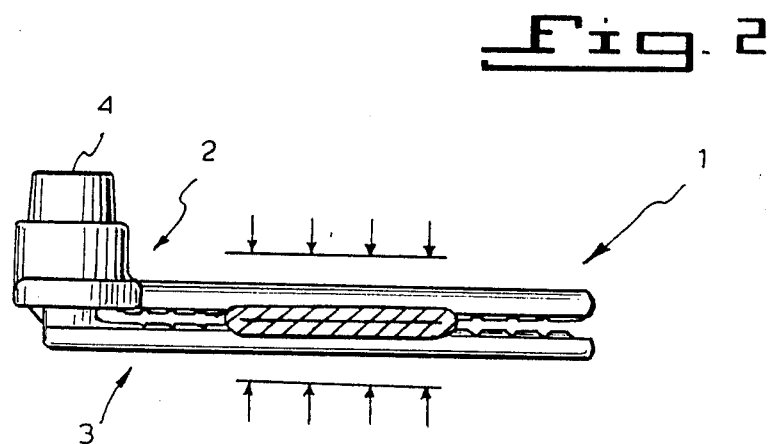
FIG. 2 is an elevational side view of the surgical clamping device of the present invention which is characterized by a clamping pressure distribution that is truly uniform along the length of the closed clamping members.
Figure 3A:
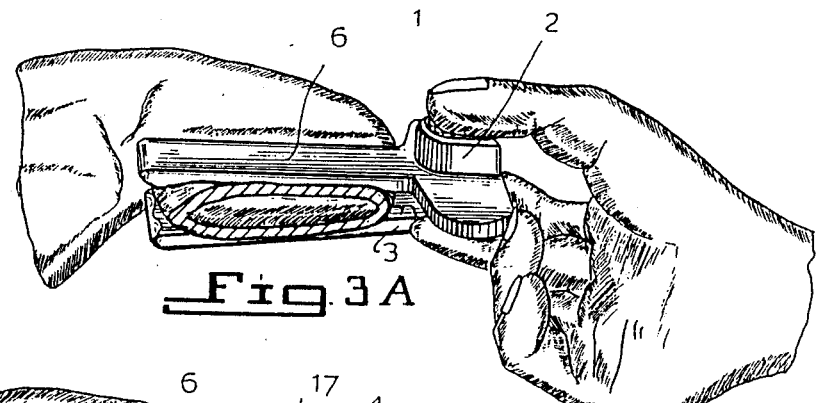
FIG. 3A is an elevated side perspective view of the surgical clamping device of the present invention, shown positioned on the end of an open intestine during a surgical procedure, with the clamping members disposed in the open locked position.
Figure 3B:
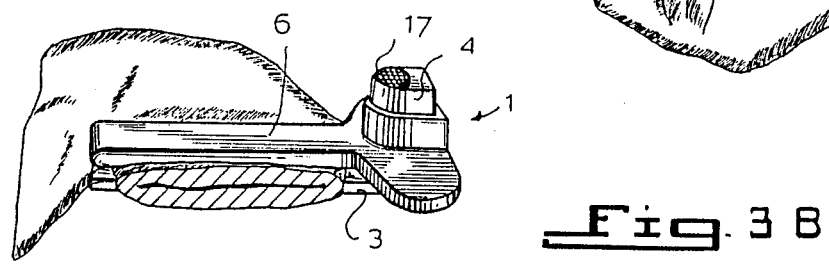
FIG. 3B is an elevated side perspective view of the surgical clamping device of the present invention, shown clamped on the open end of cut intestine, with the clamping members disposed in a parallel closed unlocked position.
Figure 4A:
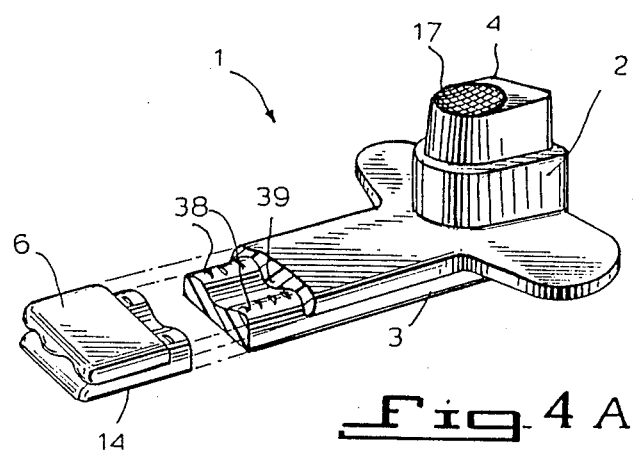
FIG. 4A is a perspective view of the surgical clamping device of the present invention, shown partially cut-away to illustrate the clamping surface thereof.
Figure 4B:
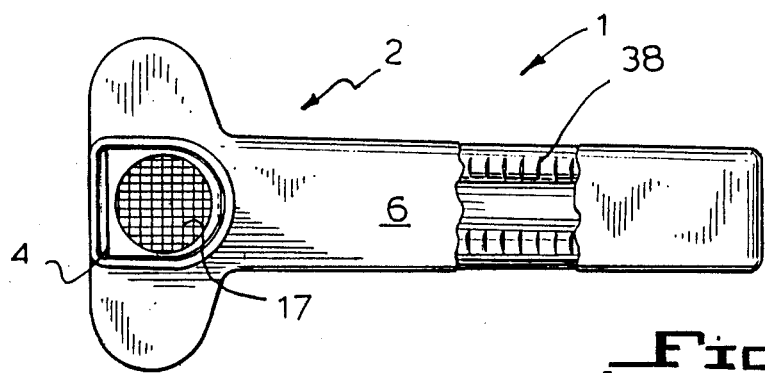
FIG. 4B is a top plan view of the surgical clamping device of the present invention, in the normal closed position, shown partially cut-away to illustrate the lower surface thereof.
Figure 4C:
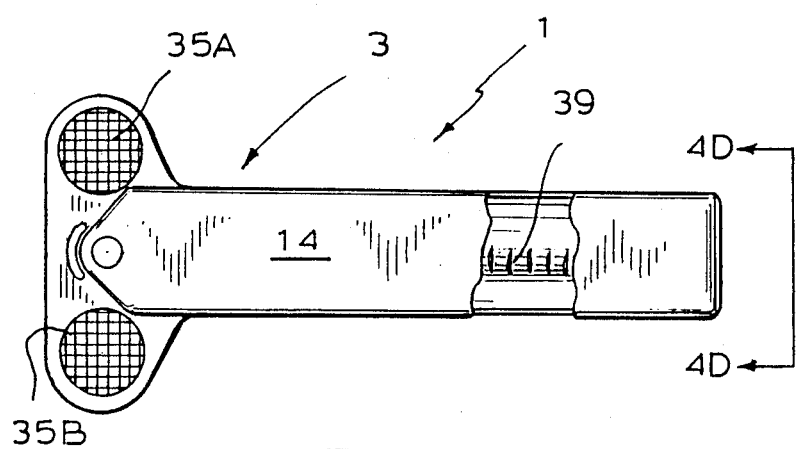
FIG. 4C is a bottom plan view of the surgical clamping device of the present invention, shown partially cut-away to illustrate the upper clamping surface thereof.
Figure 4D:
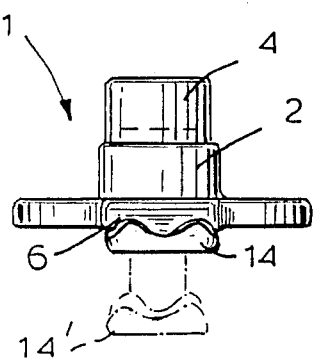
FIG. 4D is an elevational end longitudinal view of the surgical clamping device of FIGS. 4A to 4C taken along line 4D—4D showing in (phantom lines) the lower jaw in the fully open (locked) position.
Figure 5:
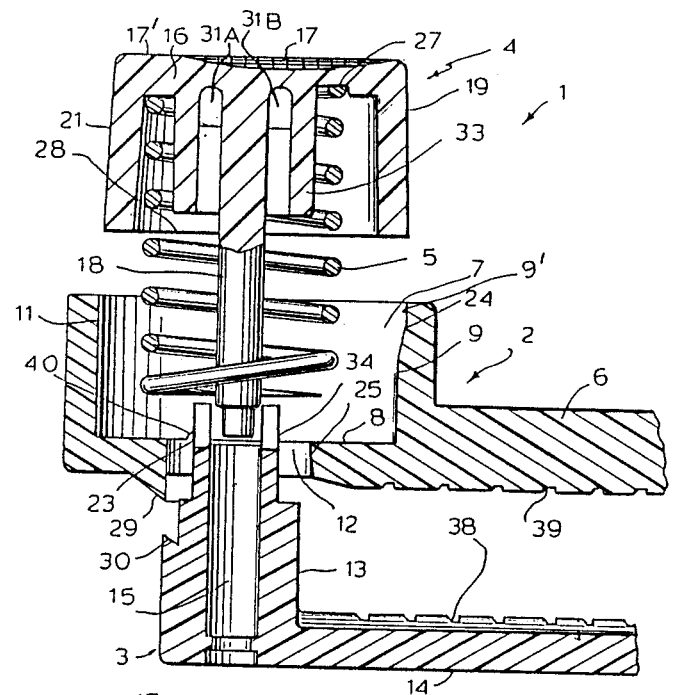
FIG. 5 is an exploded elevational side view of the surgical clamping device of the present invention, showing the clamp cap, spring means, clamp housing, and clamp base.

Referring to FIGS. 2, 3A, 3B, 4A, 4B, 4C, 4D, 5, 6, 6A, 7A, and 7B, in particular, the surgical clamping device 1 of the present invention is shown comprising a clamp housing 2, a clamp base 3, a clamp cap 4 and a spring biasing means 5.

The clamp housing 2 has a housing cavity 7 formed at one end thereof. A first clamping member 6 is connected to and projects away from the housing cavity 7. The housing cavity 7 is defined by a bottom wall 8, a front wall 9, side walls 10A and 10B, a rear wall 11 forming together an interior housing wall-configuration. The bottom wall 8 has an aperture 12 formed therethrough and the housing cavity 7 has a front end and a rear end. Hereinafter, the front end refers to the direction toward the distal end of the clamping members and the rear end refers to the direction away from the distal ends thereof.

The clamp base 3 has a base post 13 which orthogonally projects from the body of the clamp base 3. In the preferred embodiment, the body of the clamp base 3 forms a second clamping member 14. The base post 13 has a bore 15 formed therethrough and the base post 13 passes through the bottom wall aperture 12 of the housing when the device is fully assembled.

The clamp cap 4 has a cap portion 16 which has a top recess formed therein, and a stem portion 18 which orthogonally projects downwardly from the cap portion 16. The cap portion 16 has downwardly projecting front, side and rear walls, 19, 20A and 20B, and 21, respectively, whereby the cap wall-configuration formed thereby is geometrically similar to the housing wall-configuration described hereinabove.

Figure 6:
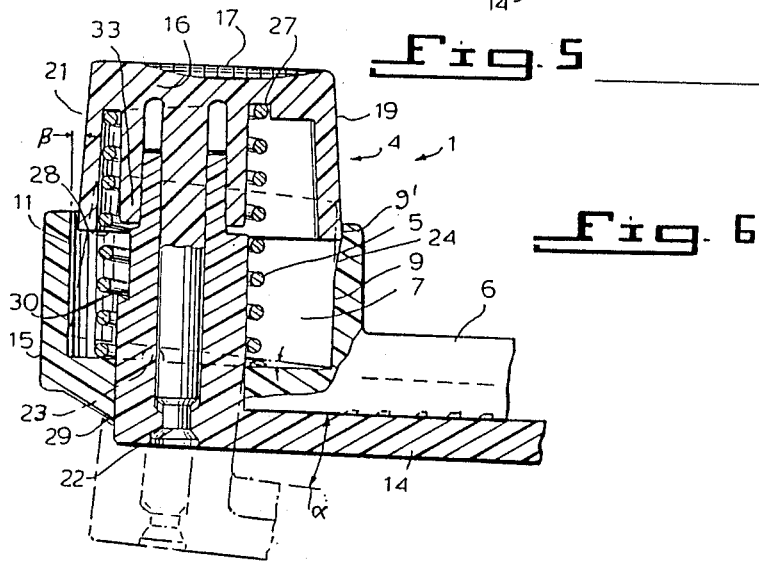
FIG. 6 is a side cross-sectional view of the surgical clamping device of the present invention shown in the closed (unlocked) position with the cap in its normal position above the housing cavity, and also shown (in phantom lines) in the open locked position with the cap disposed within the housing cavity and the lower and upper clamping member disposed in an open position.
Figure 6A:
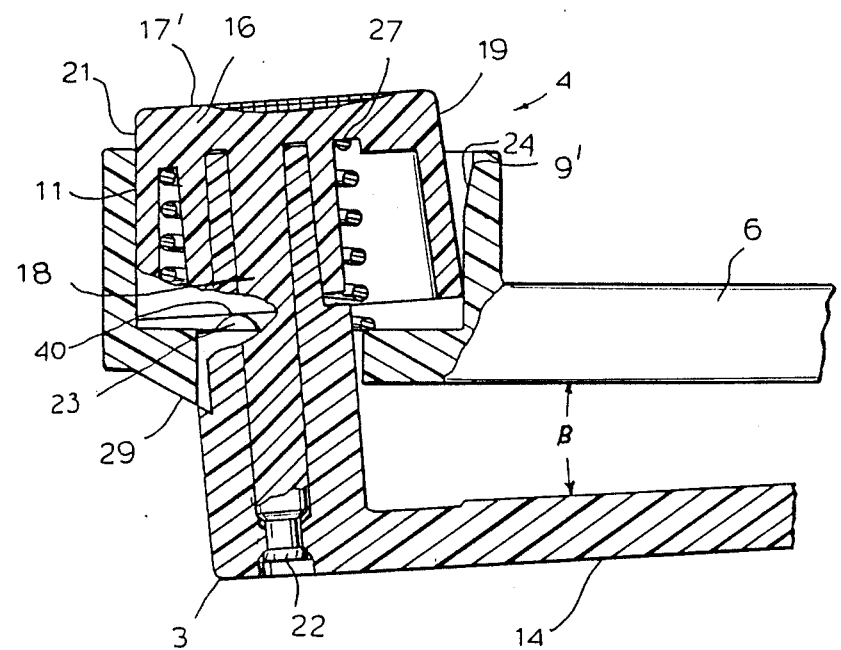
FIG. 6A is a side cross-sectional view of the surgical clamping device of the present invention shown in the open locked position with the cap disposed within the housing cavity.

In a preferred embodiment, the biasing means is the spring 5 which is disposed, within the housing cavity 7 about the base post 13 as illustrated in FIG. 6. The coefficient of stiffness or compliance of the spring 5 is selected so that the force (e.g. at least 10 lbs.) exerted on the intestinal lumen (i.e. bowel) is sufficient to occlude the lumen.

The cap stem 18 is inserted through the bore 15 in the base post 13, and is staked or heat-stamped to form an enlarged flange 22 at the distal end of the cap stem 18 in order to prevent withdrawal of the cap stem 18 from the bore 15. The cap 4 is retractably insertable into the housing cavity 7 by pressing down on the cap recess 17 with one's thumb. Notably, the downward movement of the cap 4 in the housing cavity 7 causes the cap wall 21 to become tilted and flush with the adjacent housing wall 11 against the biasing force of the spring 5 when the surgical clamping device is in any position other than the open position (which is illustrated in phantom lines in FIG. 6, in particular). This feature of the present invention, thus provides a spring-loaded, push-button clamping device having a simple and reliable operation.

To provide relative tilting for opening and/or closing of the clamping members 6 and 14 during opening and closing operations, the clamp housing 2 also includes in the preferred embodiment, a tilt fulcrum means 23, an angle ramp surface 24, a tapered wall 25 formed about the front lip of the bottom wall aperture 12, and a vertical rear wall surface 11. The cap 4, is provided with a tilted spring seat 27. Notably, however, the titled spring seat feature is not essential to the operation of the basic design of the surgical clamping device hereof, and is provided for the purpose of making it easier to lock clamping members in the lock (open) position.

Figure 7A:
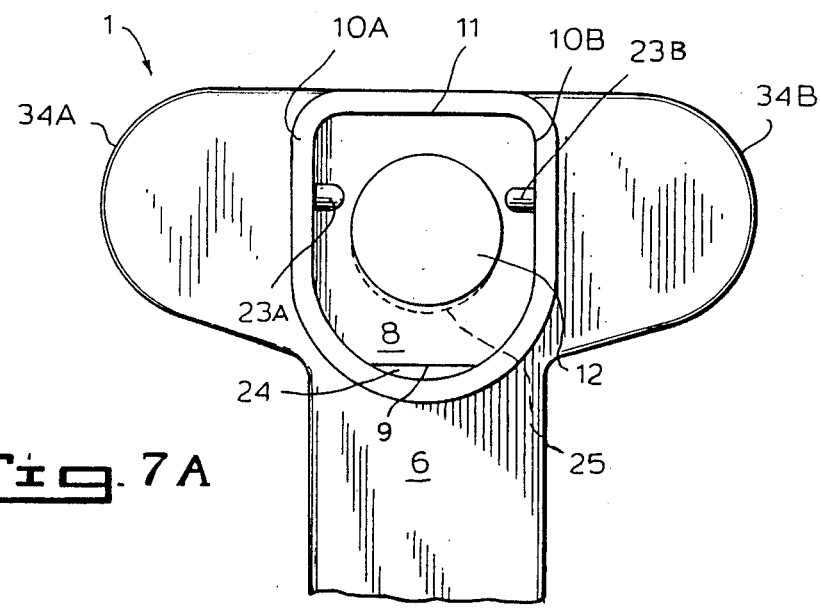
FIG. 7A is a top plan view of the surgical clamping device of the present invention showing the housing with the clamp cap and spring means removed therefrom.
Figure 7B:
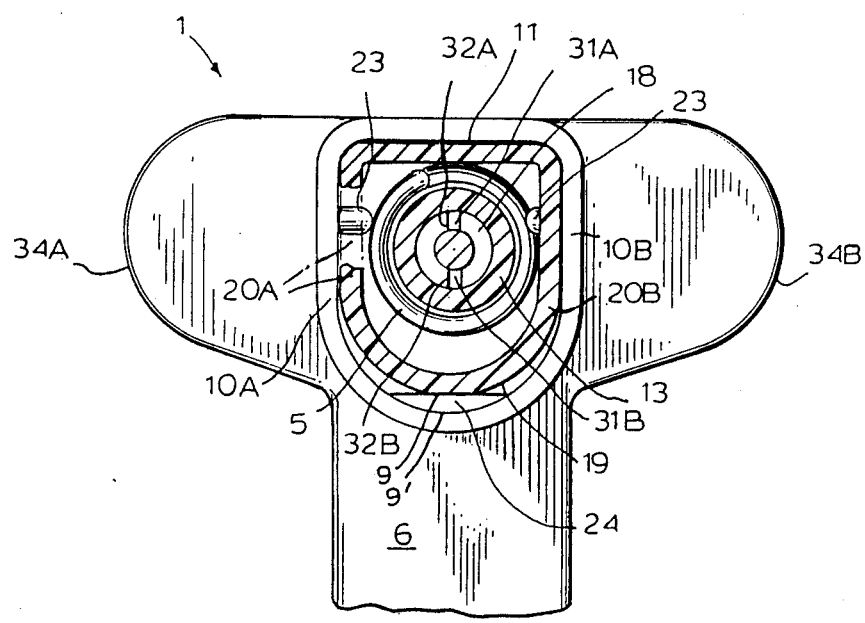
FIG. 7B is a top plan cross-sectional view of the surgical clamping device of the present invention, showing a cross-section of the housing base post, spring means and cap stem during opening cycle.
Figure 10A:
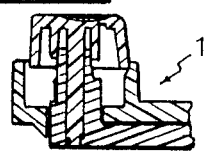
FIG. 10A is an elevated cross-sectional side view of the surgical clamping device of the present invention shown in FIG. 9A.
Figure 10B:
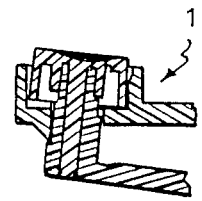
FIG. 10B is an elevated cross-sectional side view of the surgical clamping device of the present invention shown in FIG. 9B.
Figure 10C:
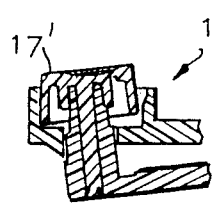
FIG. 10C is an elevated cross-sectional side view of the surgical clamping device of the present invention shown in FIG. 9C.

In particular, the tilt fulcrum means 23 is disposed in the housing cavity 7 and preferably comprises a first and second fulcrum means 23A and 23B, each realized in the form of a small, spaced apart, cylindrical or apical structure such as a pyramidal structure, which are disposed on the rear portion of the housing bottom wall 8, as illustrated in FIGS. 7A and 7B in particular. As will be described in greater detail hereinbelow, the fulcrum means 23A and 23B serves to provide cantilever (i.e. tilting) action to the cap stem 18 and base post 13 subassembly, with respect to the clamp housing 2, about a cap-fulcrum pivot point 40 located at the apex of each fulcrum means 23A and 23B. Notably, this cantilever action occurs when the bottom edge 28 of cap side walls 20A and 20B contacts the top surface of fulcrum means 23A and 23B, as illustrated in FIGS. 10B and 10C in particular, and FIG. 6 in phantom lines.

The angle ramp surface 24 is preferably realized by a tapered surface formed at the upper portion of the housing front wall 9', and serves to force the top of the cap stem 18 and base post 13 subassembly to tilt away from the front wall 9' as the front end of the cap recess 17 is depressed. The cap front wall 19 engages the angle ramp surface 24 when brought into contact with the same, and the cap portion 16 is pushed down into the housing cavity 7.

In the preferred embodiment, the tilted spring seat 27 is formed as a circular groove in the underside of the cap portion 16 concentrically formed about the axis of the cap stem 18, but can alternatively be formed in the housing bottom wall 8 concentrically about aperture 12. The tilted spring seat 27 causes the rear portion of the spring to be under higher compressional forces than the front portion thereof when the cap portion 16 is pressed down into the housing cavity 7. This uneven set of forces acting on the cap 4 about the cap-fulcrum pivot point 40, causes the cap and base subassembly to tilt thereabout, as a lever on a fulcrum 23A and 23B, and to remain in a locked position.

The tapered wall 25 formed about the front lip of the bottom wall aperture 12 serves to provide clearance between the base post 13 and the aperture 12 to allow relative tilting of base post 13 and cap stem 18 subassembly with respect to the bottom wall 8. As indicated in FIGS. 9B to 9D, this relative tilting occurs during movement of the distal ends of the second clamping member 14 towards the distal ends of the first clamping member 6 during the closing operation, which is more fully illustrated in FIGS. 10B and 10D.

The rear wall 21 of the cap 4 and the rear wall 11 of the housing 2 are shaped and spaced apart as to provide clearance to allow the cap portion 16 and base post 13 and cap stem 18 subassembly to tilt away from the front wall 9' when (i) the rear of the cap 17' is pushed downwardly; (ii) the cap portion 16 is pressed down into the housing cavity 7; (iii) the bottom edge 28 of the cap side walls 20A and 20B are in contact with the fulcrum means 23A and 23B; and (iv) the cap stem 18 and base post 13 subassembly tilt on the fulcrum means 23A and 23B about the cap-fulcrum pivot point 40.

Figure 9A:
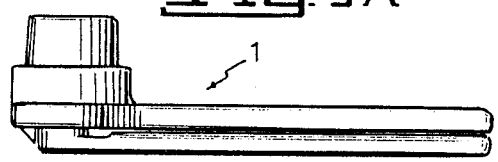
FIG. 9A is an elevational side view of the surgical clamping device of the present invention shown in the closed position.
Figure 9B:
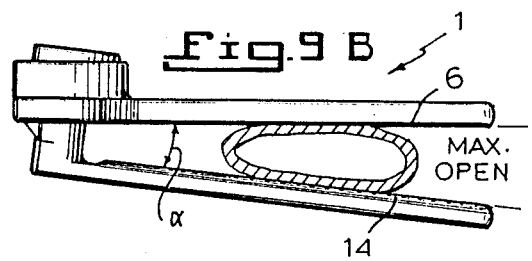
FIG. 9B is an elevational side view of the surgical clamping device of the present invention shown in the open locked position.
Figure 9C:
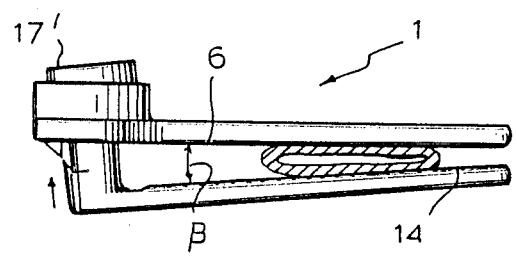
FIG. 9C is an elevational side view of the surgical clamping device of the present invention shown in the "just unlocked" stage of the closing operation of the clamping members, with an intestinal lumen interposed therebetween.
Figure 9D:
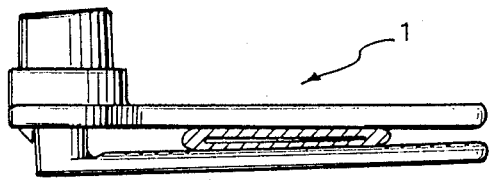
FIG. 9D is an elevational side view of the surgical clamping device of the present invention shown in a subsequent stage of the closing operation of the clamping members, with an intestinal lumen interposed therebetween.
Figure 10D:
FIG. 10D is an elevated cross-sectional side view of the surgical clamping device of the present invention shown in FIG. 9D.

In order to maintain the surgical clamping device in the open locked position as shown in FIGS. 9B and 10B, (that is when the clamping members 6 and 14 are forceably opened), the housing further includes a lock tab 29, and the base post 13 includes a lock flange 30. The lock tab 29 is disposed on the bottom side of the housing 2 adjacent the rear side of the bottom wall aperture 12, and preferably is integrally formed with the housing 2 itself. The lock flange 30 is preferably integrally formed with the rear side of the base post 13 and at a location such that the lock tab 29 and the lock flange 30 lockingly interengage when the cap portion 16 is pushed fully down into the housing cavity 7, and the bottom edge 28 of the cap side walls contact the fulcrum means 23A and 23B and the cap 4 pivots forward due to applied thumb pressure, rotating the lock flange 30 under the lock tab 29. Upon such interengagement, the first and second clamping members 6 and 14, respectively, are locked in the open position as shown in FIG. 9B and 10B.

To release the clamping members 6 and 14 from the open locked position, the rear side of the cap 17' is depressed as shown in FIG. 10C, upon which the distal ends of the clamping members first swing towards each other in one continuous motion under the biasing force of the thumb and the above-described cantilever (i.e. forced tilting) action exerted upon the cap 4.

Referring to FIG. 7B, the surgical clamping device 1 of the present invention is provided with a pair of rib members 31A and 31B which project from the underside of the cap portion 16 in the direction of the cap stem 18. In addition, the base post 13 is provided with a pair of diametrically disposed rib member receiving slots 32A and 32B formed in the upper portion of the walls of the base post 13. The rib member receiving slots 32A and 32B receive the rib members 31A and 31B, respectively, in order to prevent relative rotation between the cap 4 and the clamp base 3. The cap sidewalls 20A and 20B are received in the housing sidewalls 10A and 10B in a "slide fit" manner. This ensures that the housing, cap, and base remain in line, and the clamping jaws 6 and 14 engage accurately.

In order to prevent excessive opening deflection due to loading from spring pressure, a tubular collar 33 projecting from the underside of the cap portion 16 slides over and around the uppermost portion 34 of the base post 13, to provide a double wall for added structural integrity.

The dimensions of the angle ramp surface 24, the fulcrum means 23A and 23B, the tapered wall 25, and the shape and spacing apart of the cap rear wall 21 and the housing rear wall 11 are important in order to effect desired tilting of the base post 13 and cap stem 18 subassembly, thus the desired opening and closing operation of the clamping members. In the preferred embodiment, the dimensions have been selected so that as the front of the cap recess 17 is pushed downwardly, the cap front wall 19 engages the angle ramp surface 24 and the cap stem 18 and base post 13 subassembly tilts with respect to the front wall 9 to thereby cause the first and second clamping members 6 and 14 to be disposed at an acute angle $\beta$ (e.g. about 3°) with respect to each other. This action of angle ramp surface 24 against cap front wall 11 forces, in effect, the clamping jaws 6 and 14 to move away from each other less at their distal ends than at their proximal ends.

While being depressed at its front, the cap 4 then continues to move downwardly into the housing cavity 7 until the bottom portion 28 of the cap side walls 20A, 20B contacts the first and second spaced-apart tilt fulcrum means 23A and 23B, whereupon the lock tab 29 and lock flange 30 lockingly interengage with final downward pressure applied on cap recess 17, as illustrated in FIGS. 9B and 10B, in particular. Notably, the fulcrum means 23A and 23B are contacted only at full open and lock and release modes of operation. As illustrated in FIG. 9B, while the device is locked in this position, the cap bottom edge 28 is disposed at a first "diverging" angle $\alpha$ of about 4° with respect to the housing bottom wall 8, as are the clamping members 6 and 14. Notably, as well, this diverging angle $\alpha$ is achieved only when the device is in the lock-open position.

Figure 9E:
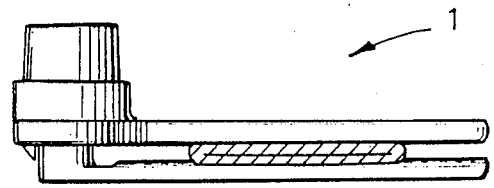
FIG. 9E is an elevated side view of the surgical clamping device of the present invention shown in the final stage of the closing operation of the clamping member on an intestine.

As illustrated in FIGS. 9B and 9C, upon pressing down the rear end of the cap 17', the cap and base subassembly is caused to undergo in a continuous motion, angular displacement whereby the first and second clamping members 6, 14 are caused to be disposed at a second or "converging" angle $\beta$ (e.g. about 3°). Notably, the converging angle $\beta$ is achieved only when the jaws are in position to close on the bowel. During this converging angular displacement of the clamping members 6 and 14, the distal ends of the clamping members move or converge towards a closed position under the biasing force of the spring, as illustrated in FIGS. 9C through 9E, and the jaws 6 and 14 become substantially parallel with the tubular structure or bowel interposed therebetween. In this condition illustrated in FIG. 9E, the spring force is in equilibrium with the resisting force of the bowel.

As illustrated in FIG. 6, the amount of angular displacement (i.e. $\alpha$) that the cap and base assembly is allowed to undergo within the housing 2, is determined by the rotation of the cap when the bottom edge 28 of the cap 4 is pressed against the fulcrum means 23A and 23B, and the jaw members 6 and 14 are urged into the open locked position.

In contrast, the angle $\beta$ is determined by (i) the surface contact between cap wall 21 and housing rear wall 11, while base post 13 is sliding through housing aperture 12 and, (ii) the sliding contact between the housing front wall 9 and the cap front wall 19. As a result of take up clearances and deflection of clamping members providing for the final parallel jaw configuration, the clamping pressure distributed along clamping members 6 and 14 is substantially uniform in the final parallel configuration.

At this juncture, it is appropriate to mention that except for when the clamping device is engaged in the lock-open position, the surgeon's thumb is fighting the spring force which is typically greater than 10 pounds. Thus, in the lock-open position, where there is no spring-resistance against the surgeon's thumb, it is much easier to apply and position the clamp accurately, as desired.

In the preferred embodiment, the housing 2 also includes first and second "wing-like" gripping tabs 34A and 34B, each of which projects from the sides of the housing cavity 7. The gripping tabs 34A and 34B each can have respective gripping recesses 35A and 35B, which provides two surfaces against which the surgical clamping device 1 can be held firmly in the hand of a surgeon or surgeon's assistant, while the thumb thereof presses on the cap recess 17 to open and/or close the surgical clamping device 1.

The opening and closing operation of surgical clamping device 1 during one complete operation cycle, is graphically illustrated in FIGS. 10A through 10D.

Referring now to FIGS. 8A through 8D in particular, the clamping surface of the present invention will be described hereinbelow. The clamping surface of the present invention is provided to the jaws of the clamping members 6 and 14, and in general, comprises a first and second corrugated surface, 36 and 37, each surface having periodically recurring peaks and valleys, and being matched with one another to establish an interlocking relationship. When the clamping members are disposed in a closed position, the peaks and valleys are aligned in the longitudinal dimension of the clamping members, and serve to substantially increase the gripping surface area thereof.

Preferably, the corrugated surface 36 and 37 are "smooth" in the geometric sense, implying that there are not discontinuities in the surface, except for the anti-slip grooves formed therein which will be described hereinafter.

In order to achieve a uniform clamping pressure in the width-wise direction of the clamping members 6 and 14, the spacing between corresponding clamping surface points on the first and second clamping members 6 and 14 is substantially equal along the entire length and width of the clamping surface, that is, when the clamping surfaces are spaced apart by the distance equal to the height of a clamped down tubular structure which is not to be traumatized. In the case of occluding intestinal lumen, the distance is typically about ⅜ of an inch, and may vary slightly from individual to individual.

In order to prevent a slippery tubular structure, such as an intestine or bowel, from slipping out from under the clamping pressure of closed clamping members and at the same time allow the intestine to be easily slipped in between the clamping members when in their open locked position as illustrated in FIGS. 9B and 10B, a plurality of specially designed anti-slip grooves 38 and 39 are formed in the peaks of the upper and lower corrugated surfaces 36 and 37, respectively. These anti-slip grooves 38 and 39 are illustrated in FIGS. 8C and 8D, in particular, and notably serve (i) to further increase the surface area of the clamping surfaces, and (ii) to provide periodic small recesses into which intestinal tissue can be compressed without traumatizing the tissue.

Referring to FIGS. 8C and 8D, each anti-slip groove 38 in the preferred embodiment has a bottom wall 39A, an inclined wall 39B, and a perpendicular wall 39C which is perpendicular (i.e. orthogonal) to the bottom wall 39A. The inclined wall 9B is disposed at an angle of about 45° from the plane of the bottom wall 39A, and facilitates sliding the intestine or other vessel between the open clamping members with a minimal degree of resistance or reacting force. On the other hand, the perpendicular wall 39C is disposed at about 90° with respect to the plane of bottom wall 39A, has a height of about 0.020 inch (but could be any value with the range of about 0.010 to about 0.050 inch), and thus creates substantially high resistance to movement of clamped vessels out from between the clamping member in the direction of the distal ends thereof. In short, this structural feature of the present invention prevents a clamped vessel from slipping out from between the jaws of the surgical clamping device 1 without the adverse effects of tissue traumatization.

Referring to FIG. 8D, a cross-sectional view of the plurality of anti-slip grooves 38 is illustrated on both the upper and lower jaws of the clamping members. In the preferred embodiment, the spacing of the parallelly disposed anti-slip grooves 38 is about 0.100–0.180 inches, but could take on one of many values falling within a range that provides desired results within a system of operating parameters including clamping pressure, vessel thickness, vessel diameter in clamped position, and the like.

The cap 4, base 3, and housing 2 of the surgical clamping device 1 of the present invention can be made of high tensile strength, injection-molded thermoplastic such as acetal or polycarbonate for example, as to thereby make the device disposable and inexpensive to manufacture. Preferably, the spring 5 is made of stainless steel, but other suitable materials may be used as well. In certain applications, the components of the surgical clamping device can be fabricated from stainless steel, and thus may permit sterilization and reuse.

Several apparent modifications to the above-described surgical clamping device and clamping surface come to mind. For example, the geometry of the clamp cap 4, clamp housing 2 an clamp base 3 can take on one of many possible forms, the present preferred embodiment thereof being shown hereinabove for purposes of description and not limitation. Therefore, instead of the cap 4 and housing cavity 7 having a substantially square geometry, other functionally equivalent geometry could replace the same to provide the desired clearances for cantilever (i.e. tilting) action of the cap and base post 13 subassembly, with respect to the housing 2.

Alternatively, the corrugated clamping surfaces 36 and 37 can be of the form of triangular ridges instead of the pseudosinusoidal waveform of the preferred embodiment illustrated in FIGS. 8A and 8B. In each case, however, the peaks of the corrugated surfaces can include the anti-slip grooves 38, as described hereinbefore.

While the particular embodiment shown and discussed above has proven to be useful in many applications, further modifications of the present invention herein disclosed will occur to persons skilled in the art to which the present invention pertains, and all such modifications are deemed to be within the scope and spirit of the present invention defined by the appended claims.

What is claimed is:

1. A surgical clamping device operable between an open and closed position for occluding anatomical tubular structures, comprising:
    (a) a first clamping member having a first jaw portion with a proximal end an a distal end, and a clamp housing fixed on the proximal end of said jaw portion, said clamp housing adapted to receive a second clamping member with a jaw portion opposite said first jaw portion of said first member and having an interior cavity with at least a front wall, a back wall, and a bottom wall, said bottom wall having an aperture formed therethrough;
    (b) a second clamping member having a second jaw portion with a proximal end and a distal end, and a clamp base fixed to the proximal end of said jaw portion, the clamp base having a base post for passage through said aperture of said bottom wall of said housing, said base post having a bore formed therethrough, and a cap stem and a cap fixed on the cap stem, said cap adapted to fit in said clamp housing, and said cap stem being received by said bore, said cap having at least a front wall arranged adjacent and proximal to said front wall of said housing and a back wall arranged adjacent and proximal to said back wall of said housing during operation of said clamping device and adapted to orient said second member jaw portion opposite said first member jaw portion, said aperture of said bottom wall of said housing allowing pivoting of said cap stem and said base post within said housing during movement of said jaw portions between an opened and a closed position;
    (c) biasing means fixed with respect to said housing and said cap to continually urge said jaws to the closed position with a force sufficient to occlude said tubular structure; and
    (d) deflection means provided on said housing and said base for causing said distal ends of said jaw portions to diverge when sid device is in the open position and for causing said distal ends of said jaw portions to converge as said device closes under the force of said biasing means whereby said jaws are substantially parallel in the closed position with said tubular structure interposed therebetween to provide uniformly distributed clamping pressure on said tubular structure.

2. The surgical clamping device of claim 1, wherein said deflection means includes an angle ramp surface formed on the front wall of said housing,
    the front wall of said cap engaging said angle ramp surface and being deflected thereby to cause said first and said second jaw portions to converge as the cap is pushed down into the housing cavity.

3. The surgical clamping device of claim 2 wherein said deflection means includes tilt fulcrum means disposed in said interior housing cavity,
    said back wall of said housing shaped to provide take up clearances to allow the back wall of said cap and base post to tilt with respect to said front wall when said cap is sliding in said housing cavity,
    whereby the cap engages the fulcrum means and pivots thereon to cause the distal ends of said jaw portions to converge.

4. The surgical clamping device of claim 3, wherein sid biasing means includes a spring having a front portion and a rear portion and said cap further comprises an underside portion, and a tilt spring seat formed about the axis of said cap stem in one of the underside of said cap and said housing bottom wall, thereby causing the rear portion of said spring to be under higher compressional forces than the front portion of said spring when said cap is pushed into said housing cavity.

5. The surgical clamping device of claim 4, wherein the dimensions of sid angle ramp, said fulcrum means, said aperture, and the shape and spacing apart of sid back cap wall and back housing wall are such that, as the cap is pushed downwardly into the housing cavity, said cap front wall engages said angle ramp surface and said cap stem and base post tilt with respect to said front wall of said housing interior cavity to thereby cause said first and second clamping members to be disposed at a first acute angle with respect to each other, said cap continuing to move downwardly into said housing cavity until the cap contacts said tilt fulcrum means, whereupon sid cap is caused to undergo in a continuous motion, an angular displacement, whereby said firs and second clamping members are caused to be disposed at a second angle greater than said first angle so that the distal ends of said clamping members diverge and lock under the biasing force of said spring.

6. The surgical device of claim 5, wherein said first angle is about 3° with the clamping members converging and said second angle is about 4° with the clamping members diverging, the overall angular displacement being about 7° total.

7. The surgical clamping device of claim 3, wherein said aperture on said bottom wall further comprises a front side and a rear side and said bottom wall of said housing further comprises a lock tab disposed on the housing adjacent the rear side of said aperture, and said base post further comprises a lock flange disposed thereon such that said lock tab and lock flange lockingly interengage by pivoting when said cap is in contact with said fulcrum means, whereby said first and second clamping members are locked in said open position.

8. The surgical clamping device of claim 3, wherein said cap further comprises a pair of rib members projecting from sid cap in the direction of said cap stem, and wherein said base post further comprises an upper portion having a pair of rib member receiving slots for receiving said rib members and preventing relative rotation between said cap stem and said base post.

9. The surgical clamping device of claim 3, wherein said bottom wall of said interior cavity further comprises a rear portion and said tilt fulcrum means comprises a first fulcrum means and a second fulcrum means disposed on the rear portion of said housing bottom wall.

10. The surgical clamping device of claim 1, wherein said clamp base, clamp base and clamp housing are formed of a rigid thermoplastic.

11. The surgical clamping device of claim 1, wherein said clamp base, clamp cap and clamp housing are formed of stainless steel.

12. The surgical clamp device of claim 1, wherein said housing further comprises opposite first and second housing sides and a first and a second gripping tab, said first gripping tab projecting from said first housing side and said second gripping tab projecting from said second housing side of said housing cavity.

13. The surgical clamping device of claim 1, wherein the first jaw portion of the first clamping member and the second jaw portion of the second clamping member include a clamping surface having a corrugated surface, and at least one peak and valley formed on said corrugated surfaces, the peak on the first clamping surface being matched with the valley on the second clamping surface to establish an interlocking relationship when said clamping members are in the closed position whereby uniform clamping pressure in the width-wise direction of said clamping members is achieved.

14. The surgical clamping device of claim 13, wherein at least one of said clamping surfaces bears a plurality of horizontally disposed grooves, each of said grooves being formed in the peak of at least one of said first and second clamping surfaces and each of said grooves having a bottom wall, an inclined wall, and a perpendicular wall, said groove facilitating sliding of tubular structures thereover towards the proximal ends of said clamping member with substantially minimal resistance, said perpendicular wall being disposed to provide substantially high resistance to movement of clamped tubular structures out from between said clamping members in the direction of said distal ends thereof.

15. The surgical clamping device of claim 14, wherein said first and second clamping surfaces have clamping surface points arranged in substantially equal spacing along the entire length and width of said clamping surfaces when said occluded anatomical tubular structure is placed therebetween.

16. The surgical clamping device of claim 15, wherein said first and said second clamping surfaces are spaced apart by about ⅛ of an inch when said device is in the closed position.

17. The surgical clamping device of claim 14, wherein said inclined wall said disposed at an angle of 45° with respect to said bottom wall.

* * * * *